United States Patent
Pang et al.

(10) Patent No.: US 10,221,407 B2
(45) Date of Patent: *Mar. 5, 2019

(54) STABILIZED RECOMBINANT EXPRESSION PLASMID VECTOR IN HAFNIA ALVEI AND APPLICATIONS THEREOF

(71) Applicants: CATHAY INDUSTRIAL BIOTECH LTD., Shanghai (CN); CATHAY R&D CENTER CO., LTD., Shanghai (CN)

(72) Inventors: Zhenhua Pang, Shanghai (CN); Naiqiang Li, Shanghai (CN); Charlie Liu, Shanghai (CN); Xiucai Liu, Shanghai (CN)

(73) Assignees: Cathay Industrial Biotech Ltd., Shanghai (CN); Cathay R&D Center Co., Ltd., Shanghai (CN)

( * ) Notice: Subject to any disclaimer, the term of this patent is extended or adjusted under 35 U.S.C. 154(b) by 132 days.

This patent is subject to a terminal disclaimer.

(21) Appl. No.: 14/992,412

(22) Filed: Jan. 11, 2016

(65) Prior Publication Data

US 2016/0201048 A1     Jul. 14, 2016

Related U.S. Application Data

(62) Division of application No. 13/795,949, filed on Mar. 12, 2013, now Pat. No. 9,234,203.

(60) Provisional application No. 61/649,719, filed on May 21, 2012.

(51) Int. Cl.
| | |
|---|---|
| *C12N 9/88* | (2006.01) |
| *C12N 15/74* | (2006.01) |
| *C07C 211/09* | (2006.01) |
| *C12P 13/00* | (2006.01) |
| *C08G 69/26* | (2006.01) |

(52) U.S. Cl.
CPC .............. *C12N 9/88* (2013.01); *C07C 211/09* (2013.01); *C08G 69/26* (2013.01); *C12N 15/74* (2013.01); *C12P 13/00* (2013.01); *C12P 13/001* (2013.01); *C12Y 401/01018* (2013.01)

(58) Field of Classification Search
None
See application file for complete search history.

(56) References Cited

U.S. PATENT DOCUMENTS

| 7,189,543 B2 | 3/2007 | Nishi et al. |
| 2010/0120105 A1 | 5/2010 | Anthony et al. |

FOREIGN PATENT DOCUMENTS

| CN | 102056889 A | 5/2011 |
| JP | 2009028045 A | 2/2009 |

OTHER PUBLICATIONS

IUPAC-IUB Joint Commission on Biochemical Nomenclature, "Guideline for Preparing Specifications Including Base Sequences and Amino Acid Sequences," Eur. J. Biochem. 138:9-37 (1984).
Martinez, J. L., "Environmental Pollution by Antibiotics and by Antibiotic Resistance Determinants," Environmental Pollution 157(11):2893-2902 (2009).
Papadakis, E.D., et al., "Promoters and Control Elements: Desiging Expression Cassettes for Gene Therapy," Current Gene Therapy 4:89:113 (2004).
Wertz, J. E., et al., "Chimeric Nature of Two Plasmids of Hafnia Alvei Encoding the Bacteriocins Alveicins A and B," J. Bacteriology 186:1598-1605 (2004).

*Primary Examiner* — Suzanne M Noakes
(74) *Attorney, Agent, or Firm* — Perkins Coie LLP; Yingli Wang

(57) ABSTRACT

One aspect of the present disclosure relates to a stabilized recombinant expression plasmid vector comprising a polynucleotide encoding an antitoxin gene which expresses a polypeptide that neutralizes a polypeptide toxic to a host cell, the toxic polypeptide being expressed by a toxin gene in the host cell, and a polynucleotide encoding a polypeptide expression product, and the stabilized recombinant expression plasmid vector is derived from a *Hafnia alvei* autonomously replicable backbone plasmid. Other aspects of the present disclosure relate to a transformant transformed with the stabilized recombinant expression plasmid vector disclosed herein, a method of producing biobased cadaverine using the transformant disclosed herein, and biobased cadaverine prepared by the method disclosed herein. Another aspect of the present disclosure relates to a polyamide formed using biobased cadaverine disclosed herein, and a composition thereof. Another aspect of the present disclosure relates to a method of preparing 1,5-diisocyanatopentane comprising preparing biobased cadaverine using the method disclosed herein and converting the biobased cadaverine to 1,5-diisocyanatopentane.

14 Claims, 7 Drawing Sheets

Specification includes a Sequence Listing.

STABILIZED RECOMBINANT EXPRESSION PLASMID VECTOR IN HAFNIA ALVEI AND APPLICATIONS THEREOF

CROSS REFERENCE TO RELATED APPLICATIONS

This application is a divisional of U.S. patent application Ser. No. 13/795,949, filed Mar. 12, 2013, which claims the benefit of U.S. Provisional Patent Application No. 61/649,719, filed May 21, 2012, which is incorporated by reference as if fully set forth herein.

BACKGROUND

Cadaverine is a platform chemical involved in the production of various products. Bio-based production of cadaverine has gained research interest since the 1980s. Cadaverine can be synthesized via decarboxylation of lysine in microorganisms. Currently, biosynthesis of cadaverine is performed using two strategies: fermentative production or in vitro enzyme catalysis.

In a fermentative production of L-lysine approach, a lysine decarboxylase gene is added to a lysine producing bacteria strain (e.g. *Corynebacterium glutamicum* and *Escherichia coli* (*E. coli*)) to extend the lysine biosynthesis pathway to a cadaverine biosynthesis pathway. However, the reported cadaverine yield is lower than the lysine yield for other *Corynebacterium glutamicum* strains lacking the lysine decarboxylase gene. Such low yield may be due to the toxicity of the cadaverine product to the producing bacterial strain.

Alternatively, bacteria can be engineered or induced to produce lysine decarboxylase for the in vitro enzyme catalysis. One strategy involves inducing expression of a chromosomally encoded lysine decarboxylase gene in an un-engineered *Hafnia alvei* (*H. alvei*) strain. However, the reported yield of the enzyme is low. Another strategy involves engineering recombinant strains. For example, Japanese companies (JP2009028045, U.S. Pat. No. 7,189,543, CN102056889) have reported the construction of *E. coli* recombinant strains that over-express lysine decarboxylase and utilize either whole cell or cell lysate for catalysis. However, expression of large amounts of polypeptides that are toxic to the host cell causes expression plasmid instability over serial passage. Antibiotics are required in the medium to ensure plasmid stability during the culture.

Use of antibiotics may cause development of antibiotic resistant bacteria, and maintains high levels of antibiotic resistant microorganisms in the environment. See, e.g. Martinez, "Environmental pollution by antibiotics and by antibiotic resistance determinants," Environmental Pollution (2009), Vol. 157, Issue 11, 2893-2902. However, antibiotic resistant bacteria potentially pose health and/or environmental hazards. Thus, there remains a need for a more effective recombinant plasmid vector that can remain stable through multiple rounds of serial passage without antibiotic selection.

DETAILED DESCRIPTION

Figure 1:
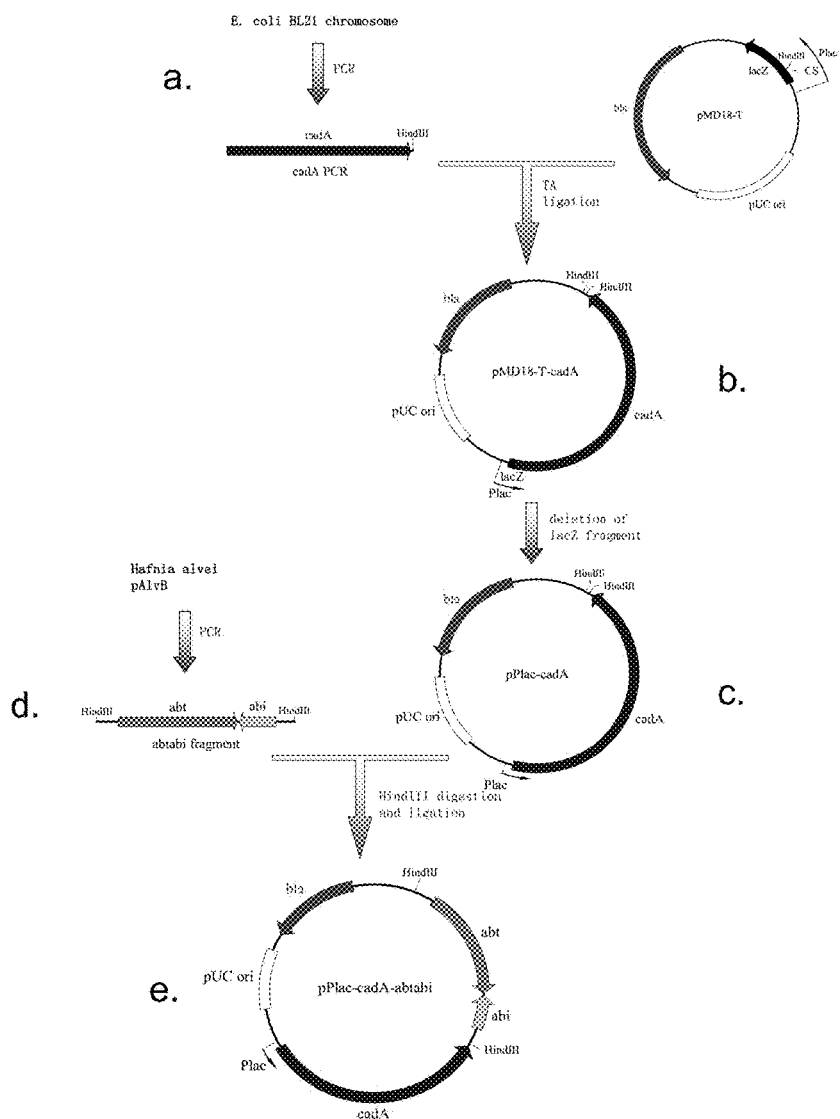
FIG. 1 shows the construction of the pPlac-cadA-abtabi recombinant expression plasmid vector as discussed in Example 1. a) cadA PCR product produced using the *E. coli* BL21 chromosome as a template; b) plasmid pMD18-T-cadA produced by ligation of the cadA PCR product to the pMD18-T vector, wherein the short lacZ fragment was located 5' to the cadA gene; c) pPlac-cadA plasmid after deletion of the lacZ fragment; d) abt/abi PCR product with HindIII sites amplified using *H. alvei* pAlvB as a template, the PCR product was then ligated to a pMD18-T vector containing a HindIII restriction site; and e) pPlac-cadA-abtabi recombinant expression plasmid produced by HindIII digestion and subsequent ligation of fragments from pPlac-cadA and the pMD18-T vector containing the abt/abi fragment.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

The abbreviations used for the amino acids, peptides, base sequences, and nucleic acids in the present disclosure are based on the abbreviations specified in the IUPAC-IUB Communication on Biochemical Nomenclature, Eur. J. Biochem., 138: 9 (1984), "Guideline for Preparing Specifications Including Base Sequences and Amino Acid Sequences" (United States Patent and Trademark Office), and those commonly used in this technical field.

A "nucleotide sequence," "polynucleotide" or "DNA molecule" as contemplated by the current disclosure, may include double strand DNA or single strand DNA (i.e., a sense chain and an antisense chain constituting the double strand DNA), and a fragment thereof. As used herein, "a fragment thereof" means a part of the nucleotide sequence that encodes a peptide which provides substantially the same function as the peptide encoded by the whole nucleotide sequence. For example, a polynucleotide encoding an antitoxin gene expresses a polypeptide that neutralizes a toxin polypeptide. A fragment of the polynucleotide encoding the antitoxin gene expresses a polypeptide that can neutralize the toxin polypeptide, which provides substantially the same function as the polypeptide encoded by the whole sequence of the polynucleotide encoding the antitoxin gene. Similarly, a fragment of a polynucleotide encoding a toxin gene expresses a polypeptide that is toxic to a cell substantially the same as the toxin polypeptide expressed by the whole sequence of the polynucleotide encoding the toxin gene.

Nucleotide sequences, polynucleotides or DNA molecules as used herein are not limited to the functional region, and may include at least one of an expression suppression region, a coding region, a leader sequence, an exon, an intron and an expression cassette (see, e.g. Papadakis et al., "Promoters and Control Elements: Designing Expression Cassettes for Gene Therapy," Current Gene Therapy (2004), 4, 89-113). Further, examples of nucleotide sequences or polynucleotides may include RNA or DNA. A polypeptide containing a specific amino acid sequence and a polynucleotide containing a specific DNA sequence may include fragments, homologs, derivatives, and mutants of the polynucleotide. Examples of mutants of a nucleotide sequence or polynucleotide (such as mutant DNA), include naturally occurring allelic mutants; artificial mutants; and mutants having deletion, substitution, addition, and/or insertion. It should be understood that such mutants encode polypeptides having substantially the same function as the polypeptide encoded by the original non-mutated polynucleotide.

One aspect of the invention relates to a stabilized recombinant expression plasmid vector comprising:

a polynucleotide encoding an antitoxin gene which expresses a polypeptide that neutralizes a polypeptide toxic to a host cell, the toxic polypeptide being expressed by a polynucleotide encoding a toxin gene in the host cell, a polynucleotide encoding a polypeptide expression product, wherein the stabilized recombinant expression plasmid vector is derived from an autonomously replicable backbone plasmid of a host cell.

In certain embodiments, the toxin gene is chromosomally encoded in the genome of the host cell.

In certain embodiments, the stabilized recombinant expression plasmid vector further comprises the polynucleotide encoding the toxin gene.

In certain embodiments, the polynucleotide encoding the toxin gene and/or the polynucleotide encoding the antitoxin gene is recombinant.

In certain embodiments, one or more genes of the toxin gene, antitoxin gene and polypeptide expression product gene are further optimized using codon optimization technology to provide better expression of the corresponding polypeptides in the host cell. For example, an optimized toxin gene may comprise a DNA sequence optimized to provide a better expression of the toxin polypeptide compared to SEQ ID NO:1 or SEQ ID NO:3. In certain embodiments, the antitoxin gene comprises a DNA sequence further optimized to provide a better expression of the antitoxin polypeptide compared to SEQ ID NO:2 or SEQ ID NO:4. In certain embodiments, the polypeptide expression product gene comprises a DNA sequence further optimized to provide a better expression of the polypeptide expression product compared to SEQ ID NO:5 or SEQ ID NO:6.

Codon optimization is a technique to maximize the protein expression in a host cell by increasing the translational efficiency of gene of interest. DNA sequence of nucleotides of one species is optimized into DNA sequence of nucleotides of another species. A DNA sequence is broken into triplets (codons). The codons of low frequency of an amino acid are replaced with codons for the same amino acid but of high frequency in the host cell. Accordingly, the expression of the optimized DNA sequence is improved in the host cell. See, e.g. www.guptalab.org/shubhg/pdf/shubhra_codon.pdf for an overview of codon optimization technology, which is incorporated herein by reference in its entirety.

As used herein, a toxin/antitoxin gene pair has two genes, one is a toxin gene which expresses a polypeptide toxic to a host cell, and the other is an antitoxin gene which expresses a polypeptide that neutralizes the toxic polypeptide in the host cell.

Certain prokaryotes have one or more chromosomally encoded toxin genes. Certain prokaryotes contain endogenous plasmids that encode specific toxin/antitoxin gene pairs that play a role in maintenance of the genetic information and response to stress. (See, Wertz et al. "Chimeric nature of two plasmids of *Hafnia alvei* encoding the bacteriocins alveicins A and B." Journal of Bacteriology, (2004) 186: 1598-1605.) In either case, as long as the cell has one or more plasmids comprising antitoxin gene, the toxin is neutralized by the antitoxin that is continuously expressed by one or more plasmids to keep the cells alive. In certain prokaryotes, the antitoxin protein degrades faster than the toxin protein. If the plasmid comprising the antitoxin gene is lost from the cell, the toxin protein will exist longer than the antitoxin protein in the cell and kill or inhibit the growth of the cell. Therefore, plasmid comprising the antitoxin or the toxin/antitoxin gene is preferably maintained to keep the host cell alive.

Examples of the toxin/antitoxin gene pair include, without limitation, abt/abi gene pair and aat/aai gene pair, and fragments thereof. In certain embodiments, the toxin gene comprises a DNA sequence of SEQ ID NO:1, or SEQ ID NO:3. In certain embodiments, the antitoxin gene comprises a DNA sequence of SEQ ID NO:2, or SEQ ID NO:4.

As used herein, the term "host cell" means a microorganism cell that can be transformed with a stabilized recombinant express plasmid vector. An example of a host cell includes, without limitation, *Hafnia alvei* (*H. alvei*).

In certain embodiments, the host cell is free of endogenous plasmid either in its native form or by removing any endogenous plasmid. The term "cure" as used herein means to remove endogenous plasmid from the host cell. The resulting endogenous plasmid-free host cell is referred to as a "cured" host cell.

In certain embodiments, the host cell may be selected from any of the *H. alvei* strains, for example, endogenous plasmid-free *H. alvei* strains, *H. alvei* strains having pAlvA plasmids and the cured strains thereof (pAlvA⁻ strains), and *H. alvei* strains having pAlvB plasmids and the cured strains thereof (pAlvB⁻ strains).

In certain embodiments, the host cell is an industrial strain suitable to be used in industrial-scale or large-scale production. For example, industrial strains may be cultivated in a fermenter. The scale of culture may range from hundreds of liters to millions of liters. On the contrary, a laboratory strain usually is cultivated in a few liters or less. In certain embodiments, an industrial strain may grow in a simpler or more economical medium than laboratory strains.

A polypeptide expression product is a polypeptide produced by a host cell. Examples of polypeptide expression products include, without limitation, any polypeptide expression product that can be produced by *E. coli.*, e.g. enzymes such as decarboxylases, hydrolases, and phosphorylase. In one embodiment, the decarboxylase is amino acid decarboxylase, e.g. lysine decarboxylase, tyrosine decarboxylase, arginine decarboxylase, ornithine decarboxylase, and glutamate decarboxylase. In another embodiment, a polynucleotide encoding a lysine decarboxylase comprises a haldc gene, a cadA gene, or a fragment thereof. In another embodiment, the polynucleotide encoding a lysine decarboxylase comprises a DNA sequence of SEQ ID NO:5, or SEQ ID NO:6. In another embodiment, the hydrolase is a N-glycosidase or a O-glycosidase, examples include, without limitation, glucosidase, α-glucosidase, β-glucosidase, mannosidase, α-mannosidase, β-mannosidase, fructosidase, β-fructosidase, xylosidase, α-xylosidase, β-xylosidase, galactosidase, α-galactosidase, β-galactosidase, lactase, amylase, α-amylase, β-amylase, myrosinase, chitinase, sucrase, maltase, invertase, hyaluronidase, and neuraminidase. In another embodiment, a polynucleotide encoding a β-galactosidase comprises lacZ gene or a fragment thereof.

An autonomously replicable backbone plasmid of a host cell may be any plasmid that can replicate in the host cell. In one embodiment, the stabilized recombinant plasmid is derived from a backbone plasmid that can replicate in *H. alvei*. Examples of the backbone plasmids include, without limitation, backbone plasmids that can replicate in *E. coli*. strains, e.g. pUC (e.g. pUC18 and pUC19 plasmids), pBR322 and pACYC plasmids, and plasmids derived therefrom.

As used herein, a recombinant plasmid "derived from an autonomously replicable backbone plasmid of a host cell" means the recombinant plasmid is constructed by inserting one or more polynucleotides encoding an antitoxin gene, one or more polynucleotides encoding a toxin gene, and/or one or more polynucleotides encoding a polypeptide expression product described herein, and any combination thereof, into the autonomously replicable backbone plasmid of the host cell.

Another aspect of the present disclosure relates to a transformant obtained by transforming one or more stabilized recombinant plasmid vector disclosed herein into a host cell.

As used herein, a transformant is a host cell that has been altered by introducing one or more recombinant plasmid vectors in the host cell. In certain embodiments, the transformant is obtained by introducing a recombinant plasmid vector through transformation into a host cell displaying competence to the plasmid vector.

An antitoxin gene transformant or toxin/antitoxin gene pair transformant shows improved plasmid stability compared to the same host cell transformed by a recombinant plasmid vector that does not contain an antitoxin gene or a toxin/antitoxin gene pair.

In one embodiment, the host cell is an endogenous plasmid-free *H. alvei* strain. The endogenous plasmid-free *H. alvei* strain in its native form may be plasmid-free. Alternatively, the endogenous plasmid-free *H. alvei* strain is a cured *H. alvei* strain as described supra. The stabilized recombinant plasmid vector comprises one or more antitoxin genes selected from the group consisting of abi gene, aai gene and fragments thereof, and/or one or more toxin/antitoxin gene pairs selected from the group consisting of abt/abi gene pair and aat/aai gene pair, and fragments thereof.

Another aspect of the present disclosure relates to a method of producing cadaverine comprising:
1a) cultivating a transformant comprising a stabilized recombinant expression plasmid vector disclosed herein;
1b) producing cadaverine using the culture obtained from step 1a to decarboxylate lysine; and
1c) recovering cadaverine from the reaction obtained from step 1b.

As used herein, "using the culture obtained from step 1a" may comprise further processes of the culture obtained from step 1a. For example, using a buffer solution to dilute the culture; centrifuging the culture to collect the cells; resuspending the cells in a buffer solution; or lysing the cells into cell lysate; or/and purifying lysine decarboxylase from the cell lysate.

The transformant may be cultured using a medium containing carbon sources and non-carbon nutrient sources. Examples of carbon sources include, without limitation, sugar (e.g. carbohydrates such as glucose and fructose), oil and/or fat, fatty acid, and/or derivatives thereof. The oil and fat may contain saturated and/or unsaturated fatty acids having 10 or more carbon atoms, e.g. coconut oil, palm oil, palm kernel oil, and the like. The fatty acid may be a saturated and/or unsaturated fatty acid, e.g. hexanoic acid, octanoic acid, decanoic acid, lauric acid, oleic acid, palmitic acid, linoleic acid, linolenic acid, myristic acid, and the like. Examples of derivatives of a fatty acid include, without limitation, esters and salts thereof. Examples of non-carbon sources include, without limitation, nitrogen sources, inorganic salts, and other organic nutrient sources.

For example, a medium may contain a carbon source assimilable by the transformant, optionally with one or more other source selected from the group consisting of a nitrogen source, an inorganic salt and another organic nutrient source. In certain embodiments, the weight percentage of the nitrogen source is about 0.01 to 0.1% of the medium. Examples of the nitrogen source may comprise ammonia, ammonium salts (e.g. ammonium chloride, ammonium sulfate and ammonium phosphate), peptone, meat extract, yeast extract, and the like. Examples of the inorganic salts include, without limitation, potassium dihydrogen phosphate, dipotassium hydrogen phosphate, magnesium phosphate, magnesium sulfate, sodium chloride, and the like. Examples of the other organic nutrient source include, without limitation, amino acids (e.g. glycine, alanine, serine, threonine and proline), vitamins (e.g. vitamin B1, vitamin B12 and vitamin C), and the like.

The culture may be carried out at any temperature as long as the cells can grow, and preferably at about 20 to about 40° C., or about 35° C. The culture period may be about 1, about 2, about 3, about 4, about 5, about 6, about 7, about 8, about 9, or about 10 days.

In one embodiment, the transformant is cultured in a medium containing peptides, peptones, vitamins (e.g. B vitamins), trace elements (e.g. nitrogen, sulfur, magnesium), and minerals. Examples of such medium include, without limitation, commonly known Lysogeny broth (LB) mediums comprising tryptone, yeast extract and NaCl suspended in water (e.g. distilled or deionized).

In another embodiment, step 1c of the method further comprises the following steps:
1d) separating the solid and liquid components of the reaction obtained from step 1b;
1e) adjusting the pH of the liquid component obtained from step 1d to about 14 or higher;
1f) removing water from the liquid component obtained from step 1e; and
1g) recovering cadaverine.

In step 1d, the separation of the solid and liquid components of the reaction of step 1b may be accomplished by conventional centrifugation and/or filtration.

In step 1e, the pH of the liquid component of step 1d may be adjusted by adding a base, e.g. NaOH. NaOH may be added as a solid and/or a solution (e.g. an aqueous solution).

In step 1f, the water may be removed by distillation at ambient pressure or under vacuum.

In step 1g, cadaverine may be recovered by distillation at ambient pressure or under vacuum.

Another aspect of the present disclosure relates to biobased cadaverine prepared according to the method disclosed herein.

As used herein, a "biobased" compound means the compound is considered biobased under Standard ASTM D6866.

Another aspect of the present disclosure relates to a polyamide having a structure of Structure 1:

Structure 1

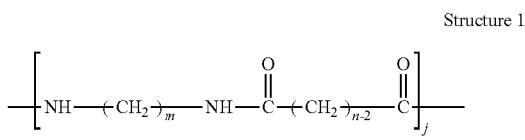

including stereoisomers thereof, wherein:
m=4, 5, 6, 7, 8, 9, 10, 11, 12, 13, 14, 15, 16, 17, 18, 19, 20, 21, or 22;
n=4, 5, 6, 7, 8, 9, 10, 11, 12, 13, 14, 15, 16, 17, 18, 19, 20, 21, or 22;
j=about 100~about 1,000,000; and
the polyamide is prepared from one or more diamines having carbon numbers of m and one or more dicarboxylic acids having carbon numbers of n, at least one of the diamines and dicarboxylic acids comprises biobased carbon under Standard ASTM D6866, and the m or n of each diamine or dicarboxylic acid can be the same or different.

In one embodiment, the diamine is biobased cadaverine, more preferably biobased cadaverine prepared according to the method disclosed herein. Examples of the dicarboxylic acids include, without limitation, $C_{10}$dicarboxylic acid, $C_{11}$dicarboxylic acid, $C_{12}$dicarboxylic acid, $C_{13}$dicarboxylic acid, $C_{14}$dicarboxylic acid, $C_{16}$dicarboxylic acid, $C_{18}$dicarboxylic acid, and any combinations thereof. In certain embodiments, all or part of the $C_n$dicarboxylic acids are biobased.

In another embodiments, the polyamide has a structure described above, wherein:
the polyamide is formed by reacting biobased cadaverine with one or more dicarboxylic acids, more preferably the biobased cadaverine is prepared according to the method disclosed herein.
n=4, 5, 6, 7, 8, 9, 10, 11, 12, 13, 14, 15, 16, 17, 18, 19, 20, 21, or 22;
j=about 100~about 1,000,000, about 1000~about 100,000, or about 1000~about 10,000; and
the dicarboxylic acids comprise biobased carbon under Standard ASTM D6866.

Another aspect of the present disclosure relates to a method of making the polyamides disclosed herein comprising
preparing biobased cadaverine as the $C_m$diamine according to the method disclosed herein.
In one embodiment, the method further comprises preparing one or more biobased $C_n$dicarboxylic acids.
In another embodiment, the method further comprises preparing the polyamide by reacting biobased cadaverine with one or more biobased $C_n$dicarboxylic acids.

Another aspect of the present disclosure relates to a composition comprising one or more polyamides disclosed herein.

In one embodiment, the diamine is biobased cadaverine, more preferably biobased cadaverine prepared according to the method disclosed herein. Examples of the dicarboxylic acids include, without limitation, $C_{10}$dicarboxylic acid, $C_{11}$dicarboxylic acid, $C_{12}$dicarboxylic acid, $C_{13}$dicarboxylic acid, $C_{14}$dicarboxylic acid, $C_{16}$dicarboxylic acid, $C_{18}$dicarboxylic acid, and any combinations thereof. In certain embodiments, all or part of the $C_n$dicarboxylic acids are biobased.

In another embodiment, the polyamide has a structure described above, wherein:
the polyamide is formed by reacting biobased cadaverine with one or more dicarboxylic acids, more preferably the biobased cadaverine is prepared according to the method disclosed herein.
n=4, 5, 6, 7, 8, 9, 10, 11, 12, 13, 14, 15, 16, 17, 18, 19, 20, 21, or 22;
j=about 100~about 1,000,000, about 1000~about 100,000, or about 1000~about 10,000; and
the dicarboxylic acids comprise biobased carbon under Standard ASTM D6866.

Another aspect of the present disclosure relates to a method of preparing 1,5-diisocyanatopentane comprising:
2a) preparing biobased cadaverine as disclosed herein; and
2b) converting biobased cadaverine obtained from step 2a to 1,5-diisocyanatopentane.

Step 2b may comprise using any known method to convert diamine into isocyanate. An example of said method is the traditional phosgene method, which includes one-step high temperature phosgene method (i.e. mixing phosgene with diamine at high temperature to obtain isocyanate), the improved two-step phosgene method, and the triphosgene method in which triphosgene is used instead of phosgene. There are also other methods that do not use phosgene as a raw material. An example of said method is hexanediamine carbonylation which uses $CO_2$ instead of phosgene: $CO_2$ is added into a solution of a primary amine and an organic base, then a proper amount of phosphorus electrophilic reagents is added into the reaction solution to start an exothermic dehydration reaction to obtain isocyanate. Another example is carbamate thermal decomposition method wherein a primary amine is converted to a carbamate, and then the carbamate is heated to decompose and generate isocyanate.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entireties, as if fully set forth herein.

EXAMPLES

Example 1—Construction of cadA Recombinant Expression Plasmid Vector cadA gene was amplified with primers 1 and 2 (primer 1, SEQ ID:NO 7: ATGAACGTTATTGCAATATT, SEQ ID:NO 8: primer 2: ACTGAAAGCTTCCACTTCCCTTG-TACGAGCT), using E. coli BL21 (purchased from Biomed) chromosomal DNA as template (FIG. 1a). The PCR product was ligated to a pUC18-derived T vector, pMD18-T (TaKaRa). The ligation product that was selected contained the cadA gene and lac promoter (Plac) positioned in the same orientation. The resulting plasmid is named pMD18-T-cadA (FIG. 1b).

pMD18-T-cadA contained a cadA gene in frame with a short lacZ fragment located at the 5' end. Subsequently, this plasmid was subjected to nucleotide deletion via site-specific mutagenesis PCR. The PCR reaction contained: 50 ng plasmid DNA, 10 pmole primer 3 (SEQ ID:NO 9: ATTCAATATTGCAATAACGTTCATAGCTGTTTCCT-GTGTG), dNTPs (0.25 mM each), 1 μL Pfu DNA polymerase (Biomed), 1 µL Taq DNA ligase (NEB), 4 µL Pfu DNA polymerase 10× buffer, 5 µL Taq DNA ligase 10× buffer and deionized water added to a total volume of 50 µL. The thermal condition was set as regular PCR. At the end of the PCR reaction, 1 µL DpnI (NEB) was added and the reaction was incubated at 37° C. for 1 hour. 100 µL of E. coli BL21 competent cells were transformed with 10 µL of the PCR reaction. Plasmids from the transformant colonies were extracted and sequenced using primer 4 (SEQ ID:NO 10: AGGAAACAGCTATGAACGTT). The expected plasmid contained a deletion of the lacZ fragment. The resulting plasmid was named pPlac-cadA, wherein the lacZ fragment to the 5' end of cadA gene was removed (FIG. 1c).

The H. alvei strain used herein contained endogenous pAlvB plasmid.

The toxin/antitoxin gene pair of the endogenous pAlvB plasmid was abt/abi gene pair. Primers 5 and 6 were designed according to the published pAlvB sequence (GenBank: AY271829) to amplify a fragment containing the abt/abi genes. The primers introduced HindIII digestion sites on both ends of the fragment (primer 5: ACTGAAAGCTT-TACTTTCATCACAAGCCTCT (SEQ ID:NO 11), primer 6: ACTGAAAGCTTAGATTCAGCGCGAGAGTGAT (SEQ ID:NO 12)) (FIG. 1d). PCR was conducted with primers 5 and 6 using pAlvB as a template. The PCR product was ligated to the pMD18-T vector. The ligation product was digested with HindIII to release a fragment of about 1.8 kb containing the abt/abi genes. The pPlac-cadA plasmid was also digested with HindIII to release a fragment of about 4.8 kb. Finally, the pPlac-cadA fragment and the abt/abi fragment were ligated together to form the recombinant expression plasmid vector, pPlac-cadA-abtabi (FIG. 1e).

Figure 2:
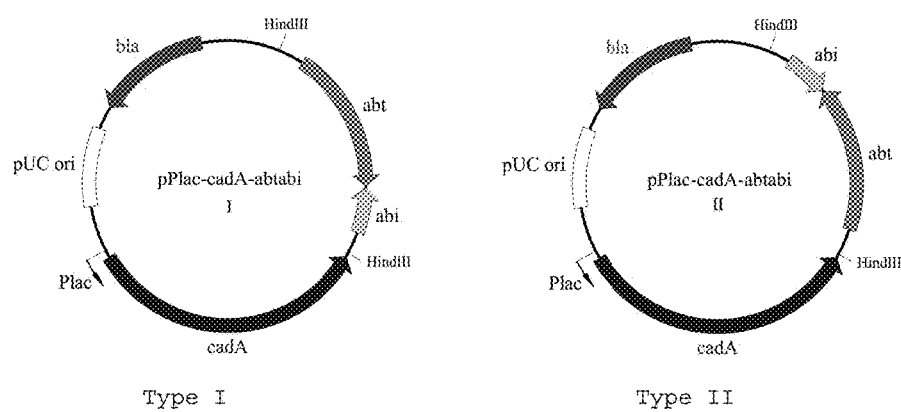
FIG. 2 shows the two possible constructions of pPlac-cadA-abtabi recombinant expression plasmid (Type I and Type II) produced according to the methods disclosed herein.

FIG. 1e shows one structure of the plasmid product for illustration purpose. One person having ordinary skill in the art would recognize, ligation of the pPlac-cadA and abt/abi fragments resulted in two types of plasmids with opposite abt/abi orientations relative to the rest of the plasmid (FIG. 2). The two orientations were identified by PCR reactions using isolated pPlac-cadA-abtabi plasmids templates. PCR reactions were conducted with either primers 1 and 5, or primers 1 and 6. The plasmid was type I plasmid (FIG. 2) when a 4 kb PCR product was produced with primers 1 and 5. The plasmid was type II plasmid (FIG. 2) when a 4 kb PCR product was produced with primers 1 and 6.

Because the H. alvei strain used herein contained endogenous pAlvB plasmid, the H. alvei strain was cured first to provide endogenous plasmid-free H. alvei strain (H. alvei$^c$). H. alvei$^c$ strain was then transformed with the new expression plasmid (pPlac-cadA-abtabi). This new recombinant expression plasmid vector showed stability after 5 or more rounds of serial subculturing without antibiotic selection.

Example 2—Curation of the Hafnia alvei Endogenous Plasmid

A H. alvei strain having endogenous pAlvB plasmid was cured to remove the endogenous plasmid. The dependence of host survival on pAlvB was relieved by expressing recombinant antitoxin using a pUC plasmid. The pUC-derived plasmid was used as a backbone plasmid because it can replicate in H. alvei and has the ability to increase copy number upon an increase in temperature. Thus, upon antibiotic selection and temperature increase, the pUC plasmid was favorably selected and the pAlvB plasmid was lost from the cell and the recombinant Abi, overexpressed by pUC, neutralized the existing endogenous Abt toxin. As a result, the H. alvei strain survived after loss of the endogenous pAlvB rather than being killed by the endogenous Abt toxin.

The abi antitoxin gene from pAlvB was amplified using primers 6 and 7 (primer 7: ACTGAAAGCTTTTTAATTGT-GTGACCACTAT (SEQ ID:NO 13)). The resulting PCR product was ligated to the pMD18-T vector (containing an ampicillin resistance gene) and was named pMD18-T-abi. The ligation product was transformed into H. alvei competent cells prepared with $CaCl_2$. The H. alvei competent cells were prepared the same way as E. coli. competent cells.

The transformant contained two plasmids in the cell: pAlvB and pMD18-T-abi. The transformant was streaked onto an LB/Amp plate and incubated at 40° C. overnight. Colony PCR was performed for the out-grown colonies with primers 5 and 6. Loss of pAlvB was confirmed by the lack of PCR product.

The next step was removal of the pUC plasmid from the pAlvB-cured H. alvei strain. The strain was streaked onto an LB plate with no ampicillin and incubated overnight at 40° C. An out-grown colony was restreaked on an LB plate and incubated at 40° C. overnight. Colony PCR was performed for the out-grown colonies with primers 6 and 7. Loss of pMD18-T-abi was confirmed by lack of PCR product as well as by lack of plasmid DNA after DNA extraction using a plasmid extraction kit (AxyPrep from Axygen).

The cured strain was named H. alvei$^c$ (Ha$^c$).

Example 3—Toxin/Antitoxin Gene Pair Stabilizes cadA Expression Plasmid in H. alvei The stability of different plasmid vectors was assayed by serially subculturing recombinant strains to non-selective medium and plating the cultures on non-selective and selective plates to estimate the total cell number and the number of plasmid-containing cells.

Single colonies of three recombinant strains: JM109/pPlac-cadA, Ha/pPlac-cadA, and Ha$^c$/pPlac-cadA-abtabi (Type II), were used to inoculate LB medium containing ampicillin (JM109 is an E. coli strain; Ha denotes unmodified H. alvei containing the endogenous pAlvB plasmid; Ha$^c$ denotes cured H. alvei lacking the pAlvB plasmid). The cultures were grown for 1 day at 35° C. (seed culture), and were then used to inoculate fresh LB medium without ampicillin at a rate of 0.1%. The subcultures were grown for 1 day ($1^{st}$ subculture). Sub-culturing was continued with the same inoculation rate and the same growth conditions ($2^{nd}$ to $5^{th}$ subculture). On each day, samples were taken from cultures and serially diluted with sterile 0.85% NaCl. 5 µL of diluted samples were spotted onto LB plates and LB/Amp plates. The plates were incubated for 1 day at 35° C. The total cell number and the number of cells that harbor the ampicillin resistant plasmid can be estimated from the number of colonies on LB and LB/Amp plates, respectively (FIG. 3 (JM109/pPlac-cadA), FIG. 4 (Ha/pPlac-cadA), FIG. 5 (Ha$^c$/pPlac-cadA-abtabi)).

Figure 3:
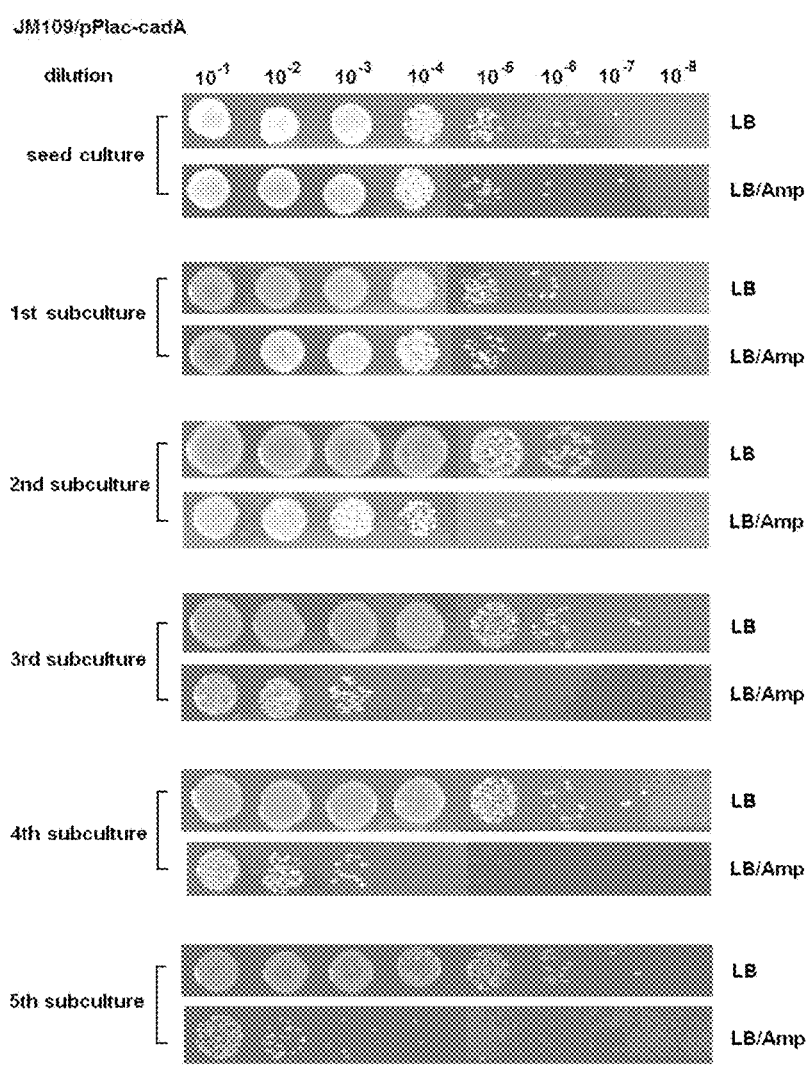
FIG. 3 shows recombinant strain JM109/pPlac-cadA colony growth on LB and LB/Amp plates after serial subculturing and serial dilution as discussed in Example 3.
Figure 4:
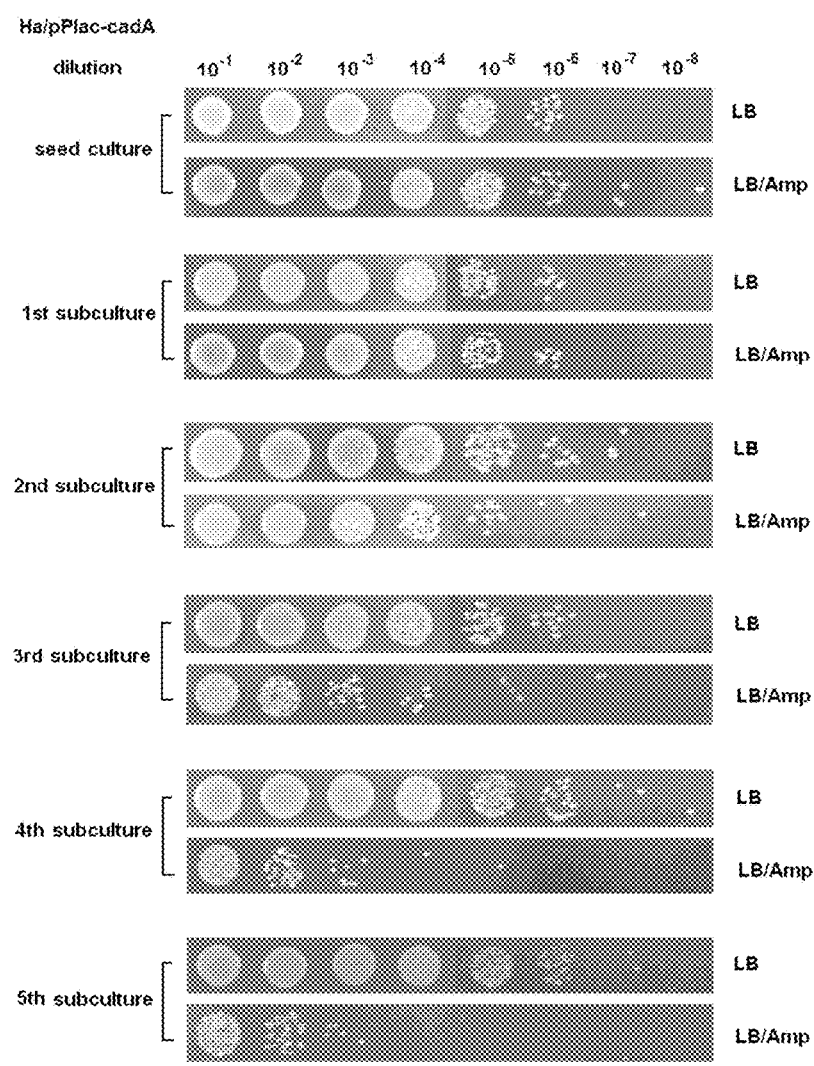
FIG. 4 shows recombinant strain Ha/pPlac-cadA colony growth on LB and LB/Amp plates after serial subculturing and serial dilution as discussed in Example 3.
Figure 5:
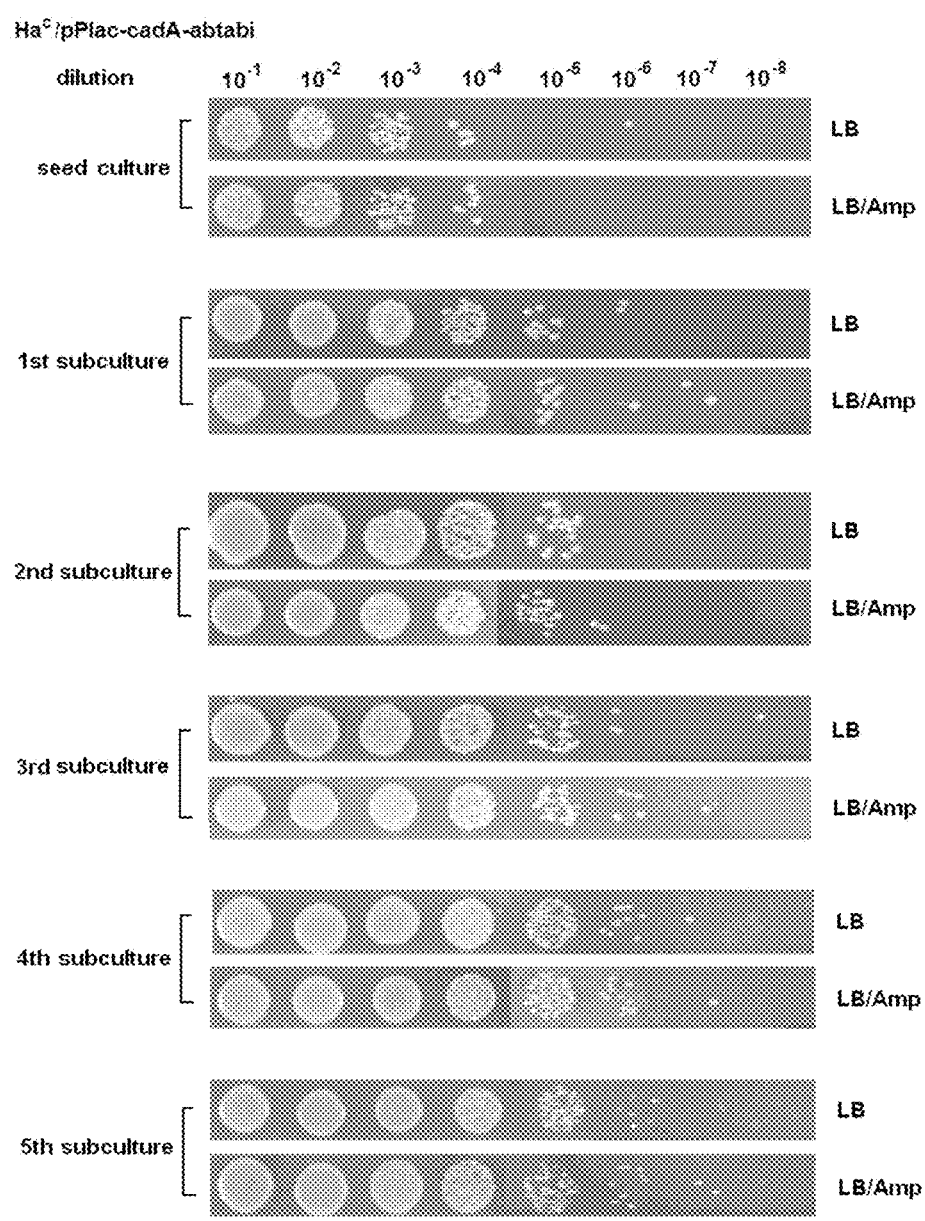
FIG. 5 shows recombinant strain $Ha^c$/pPlac-cadA-abtabi colony growth on LB and LB/Amp plates after serial subculturing and serial dilution as discussed in Example 3.

The percentage of plasmid-bearing cells decreased to approximately 1% after 2 or 3 subcultures for the JM109/pPlac-cadA and Ha/pPlac-cadA strains (FIGS. 3 and 4, respectively). However, 100% of plasmid-bearing cells remained after 5 consecutive subcultures for strain Ha$^c$/pPlac-cadA-abtabi (FIG. 5). Thus, the toxin/antitoxin genes stabilized the recombinant expression plasmid vector in H. alvei with no need of antibiotic selection.

Example 4—Stability of Plasmid pPlac-cadA in Cured H. alvei

The stability of plasmid pPlac-cadA was assayed by culturing the recombinant strain in non-selective medium and plating the culture on non-selective and selective plates to estimate the total cell number and the number of plasmid-bearing cells.

Figure 6:
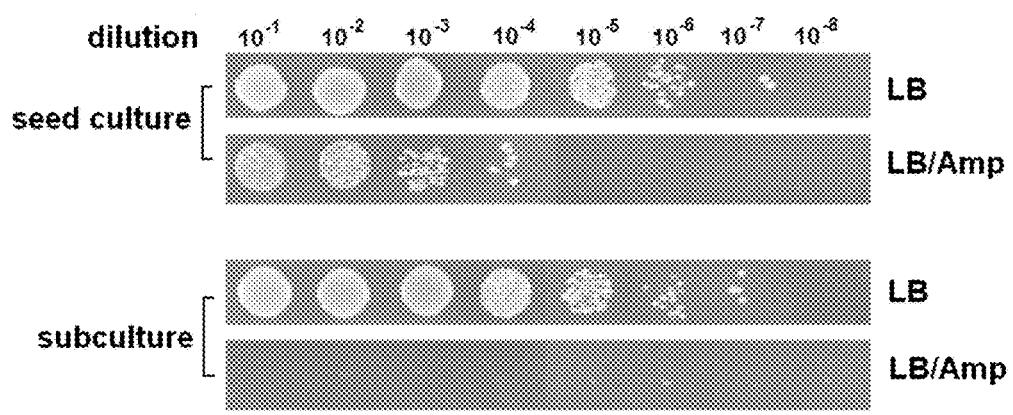
FIG. 6 shows stability of plasmid pPlac-cadA in cured *H. alvei*.

A single colony of strain Ha$^c$/pPlac-cadA was used to inoculate LB medium containing ampicillin (Ha$^c$ denotes cured *H. alvei* lacking the pAlvB plasmid). The culture was grown for 1 day at 35° C. (seed culture), and was then used to inoculate fresh LB medium without ampicillin at a rate of 0.1%. The subculture was grown for 1 day. Samples were taken from the seed culture and the subculture and serially diluted with sterile 0.85% NaCl. 5 µL of diluted samples were spotted onto LB plates and LB/Amp plates. The plates were incubated for 1 day at 35° C. The total cell number and the number of cells that harbor the ampicillin resistant plasmid can be estimated from the number of colonies on LB and LB/Amp plates, respectively (FIG. 6).

The plasmid was very unstable in cured *H. alvei*. About 0.1% of the cells retained the plasmid in the seed culture. And no plasmid-bearing cells were observed in the subculture.

Example 5—Stability of type I pPlac-cadA-abtabi plasmid in cured *H. alvei*

The stability of type I pPlac-cadA-abtabi plasmid was assayed by serially subculturing the recombinant strain in non-selective medium and plating the culture on non-selective and selective plates to estimate the total cell number and the number of plasmid-bearing cells.

Figure 7:
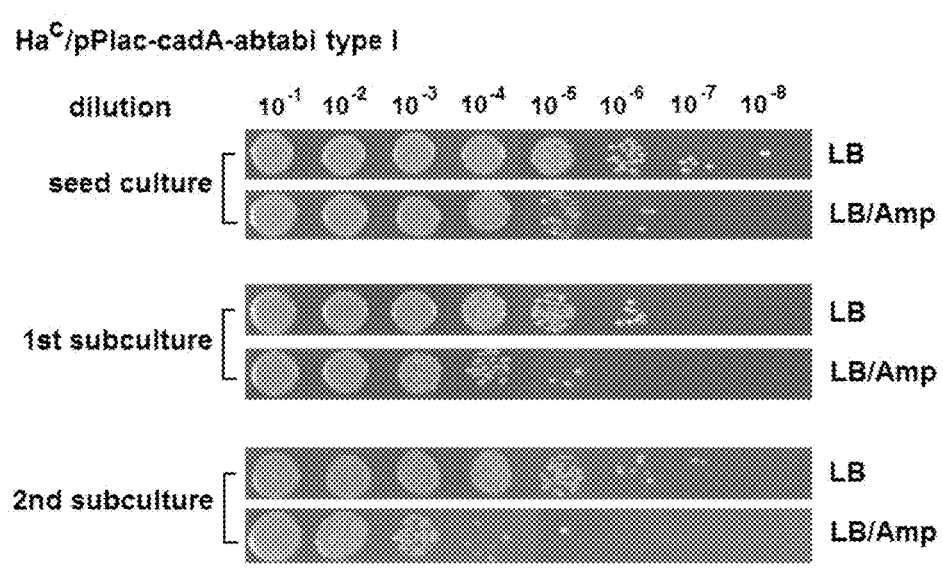
FIG. 7 shows stability of type I pPlac-cadA-abtabi plasmid in cured *H. alvei*.

A single colony of strain Ha$^c$/pPlac-cadA-abtabi (type I) was used to inoculate LB medium containing ampicillin. The culture was grown for 1 day at 35° C. (seed culture), and was then used to inoculate fresh LB medium without ampicillin at a rate of 0.1% (1$^{st}$ subculture). Sub-culturing was continued with the same inoculation rate and the same growth conditions (2$^{nd}$ subculture). Both subcultures were grown for 1 day. Samples were taken from the seed culture and the subcultures and serially diluted with sterile 0.85% NaCl. 5 µL of diluted samples were spotted onto LB plates and LB/Amp plates. The plates were incubated for 1 day at 35° C. The percentage of cells that harbor the ampicillin resistant plasmid was estimated from the number of colonies on LB and LB/Amp plates (FIG. 7).

There was a significant increase in plasmid stability when abt/abi was present on the plasmid in cured *H. alvei*. Although there was a significant loss of plasmid in the seed culture, the plasmid was not completely lost in the subcultures like pPlac-cadA was. About 1% of the cells still had the plasmid in the second subculture.

SEQUENCE LISTINGS (aat gene)
>gb|AY271828.1|: 385-1717 *Hafnia alvei* plasmid pAlvA, complete sequence
SEQ ID: NO 1

```
   1 ttgactttgt taaaagtcag gcataagatc aaaatactgt atatataaca atgtatttat
  61 atacagtatt ttatactttt tatctaacgt cagagagggc aatattatga gtggtggaga
 121 tggcaagggt cacaatagtg gagcacatga ttccggtggc agcattaatg gaacttctgg
 181 gaaagggtgg ccatcaagcg gaggagcatc agataattct gggtggagtt cggaaaataa
 241 cccgtgggc ggtggtaact cgggaatgat tggtggcagt caaggaggta acggagctaa
 301 tcatggtggc gaaaatacat cttctaacta tgggaaagat gtatcacgcc aaatcggtga
 361 tgcgatagcc agaaaggaag gcatcaatcc gaaaatattc actgggtact ttatccgttc
 421 agatggatat ttgatcggaa taacgccact tgtcagtggt gatgcctttg gcgttaatct
 481 tggcctgttc aataacaatc aaaatagtag tagtgaaaat aagggatgga atggaaggaa
 541 tggagatggc attaaaaata gtagccaagg tggatggaag attaaaacta atgaacttac
 601 ttcaaaccaa gtagctgctg ctaaatccgt tccagaacct aaaaatagta aatattataa
 661 gtccatgaga gaagctagcg atgaggttat taattctaat ttaaaccaag ggcatggagt
 721 tggtgaggca gctagagctg aagagatta cagagaaaaa gtaaagaacg caatcaatga
 781 taatagtccc aatgtgctac aggatgctat taaatttaca gcagattttt ataaggaagt
 841 ttttaacgct tacggagaaa aagccgaaaa actagccaag ttattagctg atcaagctaa
 901 aggtaaaaag atccgcaatg tagaagatgc attgaaatct tatgaaaaac acaaggctaa
 961 cattaacaaa aaaatcaatg cgaaagatcg cgaagctatc gccaaggctt tggagtctat
1021 ggatgtagaa aaagccgcaa aaaatatatc caagttcagc aaaggactag gttgggttgg
1081 cccagctatc gatataactg attggtttac agaattatac aaagcagtga aaactgataa
1141 ttggagatct ctttatgtta aaactgaaac tattgcagta gggctagctg caacccatgt
1201 caccgcctta gcattcagtg ctgtcttggg tgggcctata ggtatttag gttatggttt
1261 gattatggct ggggttgggg cgttagttaa cgagacaata gttgacgagg caaataaggt
1321 cattgggatt taa
```

(aai gene)
>gb|AY271828.1|: 1734-2069 *Hafnia alvei* plasmid pAlvA, complete sequence
SEQ ID: NO 2

```
   1 ctatatttta gcggtcacat tttttatttc aaaacaaaca gaaagaacac caataggaat
  61 tgatgtcata aaaataaaaa taaaatacaa agtcattaaa tatgtttttg gcacaccatc
 121 cttaaaaaaa cctgttttcc aaaattcttt tttcgtatat ctaagcgctg ctttctctat
 181 tagaaaccga gagaaaggaa atagaatagc gctagccaaa ccaaagattc tgagcgcaat
 241 tattttaggt tcgtcatcac cataactggc gtaaagaata caagcagcca taaagtatcc
 301 ccaaaacata ttatgtatgt aatatttcct tgtcat
```

(abt gene)
>gb|AY271829.1|: 384-1566 *Hafnia alvei* plasmid pAlvB, complete sequence
SEQ ID: NO 3

```
   1 atgagtggtg gagacggtaa aggtcacaat agtggagcac atgattccgg tggcagcatt
  61 aatggaactt cggggaaagg tggacctgat tctggtggcg gatattggga caaccatcca
 121 catattacaa tcaccggtgg acgggaagta ggtcaagggg gagctggtat caactgggt
 181 ggtggttctg tcatggtaa cggcggggc tcagttgcca tccaagaata taacacgagt
 241 aaatatccta acacgggagg atttcctcct cttggagacg ctagctggct gttaaatcct
 301 ccaaaatggt cggttattga agtaaaatca gaaaactcag catggcgctc ttatattact
 361 catgttcaag gtcatgttta caaattgact tttgatggta cgggtaagct cattgatacc
```

-continued

SEQUENCE LISTINGS

```
 421 gcgtatgtta attatgaacc cagtgatgat actcgttgga gcccgcttaa aagttttaaa
 481 tataataaag gaaccgctga aaaacaggtt agggatgcca ttaacaatga aaaagaagca
 541 gttaaggacg ctgttaaatt tactgcagac ttctataaag aggtttttaa ggtttacgga
 601 gaaaaagccg agaagctcgc taagttatta gcagatcaag ctaaaggcaa aaaggttcgc
 661 aacgtagaag atgccttgaa atcttatgaa aaatataaga ctaacattaa caaaaaaatc
 721 aatgcgaaag atcgcgaagc tattgctaaa gccttggagt ctatggatgt aggaaaagcc
 781 gcaaaaaata tagccaagtt cagtaaagga ctaggttggg ttggccctgc tatcgatata
 841 actgattggt ttacagaatt atacaaggca gtggaaactg ataattggag atcttttat
 901 gttaaaactg aaactattgc agtagggcta gctgcaaccc atgttgccgc cttggcattc
 961 agcgctgtct ggggtgggcc tgtaggtatt ttgggttatg gtttgattat ggctggggtt
1021 ggggcgttag ttaatgagac aatagttgac gaggcaaata aggttattgg gctttaa
```

(abi gene)
>gb|AY271829.1|: 1583-1918 Hafnia alvei plasmid pAlvB, complete sequence
SEQ ID: NO 4

```
  1 ctataattta gcggtcacat ttttattc aaaaaaaaca gaaataacac ctataggaat
 61 tgatgtcata aaaataaaaa ttaaatacaa agtcattaaa tatgttttg gcacgccatc
121 cttaaaaaaa ccagtttccc aaaattcttt tttcgtatat ctaagcgcgg tttctctat
181 taaaaaccga gagaaaggga ataggatagc actagccaaa ccaaagattc tgagcgcaat
241 tattttaggt tcgttatccc cataactggc gtaaagaata caaacagcca taaagtaccc
301 ccaaaacata ttatgtatat aatatttcct tgtcat
```

(E. coli gene for lysine decarboxylase (cadA))
>gb|M76411.1|ECOCADABC: 1913-4060 E.coli cadA gene, 5' cds and cadB
and cadC genes, complete cds
SEQ ID: NO 5

```
   1 atgaacgtta ttgcaatatt gaatcacatg ggggtttatt ttaaagaaga acccatccgt
  61 gaacttcatc gcgcgcttga acgtctgaac ttccagattg tttacccgaa cgaccgtgac
 121 gacttattaa aactgatcga aaacaatgcg cgtctgtgcg gcgttatttt tgactgggat
 181 aaatataatc tcgagctgtg cgaagaaatt agcaaaatga acgagaacct gccgttgtac
 241 gcgttcgcta atacgtattc cactctcgat gtaagcctga atgacctgcg tttacagatt
 301 agcttctttg aatatgcgct gggtgctgct gaagatattg ctaataagat caagcagacc
 361 actgacgaat atatcaacac tattctgcct ccgctgacta aagcactgtt taaatatgtt
 421 cgtgaaggta aatatacttt ctgtactcct ggtcacatgg gcggtactgc attccagaaa
 481 agcccggtag gtagcctgtt ctatgatttc tttggtccga ataccatgaa atctgatatt
 541 tccattcag tatctgaact gggttctctg ctggatcaca gtggtccaca caaagaagca
 601 gaacagtata tcgctcgcgt ctttaacgca gaccgcagct acatggtgac caacggtact
 661 tccactgcga acaaaattgt tggtatgtac tctgctccag caggcagcac cattctgatt
 721 gaccgtaact gccacaaatc gctgacccac ctgatgatga tgagcgatgt tacgccaatc
 781 tatttccgcc cgacccgtaa cgcttacggt attcttggtg tatcccaca gagtgaattc
 841 cagcacgcta ccattgctaa gcgcgtgaaa gaaacaccaa acgcaacctg gccggtacat
 901 gctgtaatta ccaactctac ctatgatggt ctgctgtaca caccgactt catcaagaaa
 961 acactggatg tgaaatccat ccactttgac tccgcgtggg tgccttacac caacttctca
1021 ccgatttacg aaggtaaatg cggtatgagc ggtggccgtg tagaagggaa agtgatttac
1081 gaaacccagt ccactcacaa actgctggcg gcgttctctc aggcttccat gatccacggt
1141 aaaggtgacg taaacgaaga aaccttttaac gaagcctaca tgatgcacac caccacttct
1201 ccgcactacg gtatcgtggc gtccactgaa accgctgcgg cgatgatgaa aggcaatgca
1261 ggtaagcgtc tgatcaacgg ttctattgaa cgtgcgatca aattccgtaa agagatcaaa
1321 cgtctgagaa cggaatctga tggctggttc tttgatgtat ggcagccgga tcatatcgat
1381 acgactgaat gctggccgct gcgttctgac agcacctggc acggcttcaa aaacatcgat
1441 aacagcacac tgtatcttga cccgatcaaa gtcaccctgc tgactccggg gatggaaaaa
1501 gacggcacca tgagcgactt tggtattccg gccagcatcg tggcgaaata cctcgacgaa
1561 catggcatcg ttgttgagaa aaccggtccg tataacctgc tgttcctgtt cagcatcggt
1621 atcgataaga ccaaagcact gagcctgctg cgtgtctga ctgactttaa acgtgcgttc
1681 gacctgaacc tgcgtgtgaa aaacatgctg ccgtctctgt atcgtgaaga tcctgaattc
1741 tatgaaaaca tgcgtattca ggaactggct cagaatatcc acaaactgat tgttcaccac
1801 aatctgccgg atctgatgta tcgcgcattt gaagtgctgc cgacgatggt aatgactccg
1861 tatgctgcat tccagaaaga gctgcacgt atgaccgaag aagttttacct cgacgaaatg
1921 gtaggtcgta ttaacgccaa tatgatcctt ccgtacccgc cgggagttcc tctggtaatg
1981 ccgggtgaaa tgatcaccga agaaagccgt ccggttctgg agttcctgca gatgctgtgt
2041 gaaatcggcg ctcactatcc gggctttgaa accgatattc acggtgcata ccgtcaggct
2101 gatggccgct ataccgttaa ggtattgaaa gaagaaagca aaaaataa
```

(Hafnia Alvei gene for lysine decarboxylase (haldc)
>gi|43438|emb|X03774.1| Hafnia alvei gene for lysine decarboxylase (LDC)
SEQ ID: NO 6

```
  1 atgaatatca ttgccatcat gaacgattta agcgcttatt ttaaggaaga accctgcgc
 61 gagctgcatc aagagttaga gaggaaggc ttccgtattg cttatcccaa agaccgcaac
121 gatctgctga agctgattga aaacaactcc cgcctgtgtg gcgtcatttt cgactgggat
181 aaatataacc tcgaactcag cgctgaaatc agcgagctca caaactgct gccaatttat
241 gccttcgcca ataccattc gacgcttgac gtcaacatga gcgacctgcg tcttaatgtt
301 cgcttctttg aatatgcatt aggcagcgcg caagacattg ccaccaagat ccgccaaagc
361 accgatcagt atattgatac cattctgcca ccgctgacca aggcgctgtt caaatacgtc
421 aaagaagaga aatacacagt ctgtacgccg gggcatatgg gcggaactgc gttcgataaa
481 agccctgtcg gtagcctgtt ctatgatttc ttcggtgaaa acaccatgcg ttcggatatc
541 tcgatctccg tatctgagct cggatcgctg ctcgatcata gcggcccaca ccgtgacgcc
601 gaagagtata tcgcgcgcac gttcaacgcc gatcgcagct atatcgtaac caacggaaca
```

SEQUENCE LISTINGS

```
 661 tctacggcga ataaaattgt cggcatgtat tcatctcctg ccggtgccac tattctgata
 721 gaccgtaact gccataaatc attgacccat ttgatgatga tgagcaacgt tgtccccgtc
 781 tatctgcgcc caacccgtaa cgcctacggc attttaggcg ggataccgca aagcgagttc
 841 acccgcgcca gcattgaaga gaaagtgaaa aatacgccca atgcgacatg gccggtgcat
 901 gcggtagtca ccaactctac ctatgacggc ctgttctaca ataccgaata catcaaaaac
 961 acgcttgatg ttaagtcgat tcacttcgat tcggcatggg tgccttacac caacttccat
1021 ccgatttacc aaggcaaagc agggatgagc ggtgaacgtg tgccggggaa aatcatctac
1081 gagactcagt ccacccacaa actgctggcg gcattctcgc aggcatcgat gatccacgtg
1141 aaaggtgaga tcaacgaaga aaccttcaat gaagcctata tgatgcatac ctcaacatca
1201 ccgcattacg ggatcgttgc gtcgacggaa accgcggcgg ctatgatgaa gggcaacgcc
1261 ggtaagcgtt taattaacgg ttcaattgaa cgagcgatcc gcttccgtaa agagatccgc
1321 cgcttacgta cagaatctga tggctggttc tttgacgtat ggcagccgga taacattgac
1381 gaggttgctt gctgccact caatccacgt aatgaatggc atggattccc gaacatcgac
1441 aacgatcata tgtatcttga tccgatcaaa gtcactctgc tgaccccagg tttaagcccc
1501 aatggcactc tggaagagga agggataccg cgcgtcgatcg tgtcgaaata tctggatgag
1561 cacggcatca tcgtggaaaa aaccgggcca tataacctgc tcttcctgtt tagtatcggg
1621 atcgataaaa ccaaggcgtt gagcttgttg cggcattaa ccgatttcaa acgcgtgtat
1681 gacctcaacc tgcgcgtgaa aaacgtgttg ccatcgctct ataacgaggc gcctgatttc
1741 tataaagaga tgcgaattca ggagttggct caggggattc atgctctggt gaaacaccac
1801 aatctaccag acctgatgta tcgtgcattt gaggtattac caaagctggt gatgacgccg
1861 catgatgcgt tccaagaaga agtgcgtggc aatattgagc catgtgcctt ggatgatatg
1921 ttagggaaag ttagcgccaa catgatcttg ccgtatcctc cgggtgttcc ggtggttatg
1981 ccgggagaaa tgctcactaa ggagagccgc cctgttctga gcttcttgca gatgctatgt
2041 gaaattggcg cacactatcc gggctttgaa acggatattc acggcgttca tcgtgatggt
2101 gcaacgggta aatacatggt cgtggtgctc aaacaaggcg cagatgaacc gggtgataaa
2161 ccgagtgata cggtgaagaa agcgccgggt aaaaaaccat cagcggcgaa gaagtcataa
```

```
                                                          SEQ ID: NO 7
   1 ATGAACGTTA TTGCAATATT

SEQ ID: NO 8
   1 ACTGAAAGCT TCCACTTCCC TTGTACGAGC T

SEQ ID: NO 9
   1 ATTCAATATT GCAATAACGT TCATAGCTGT TTCCTGTGTG

SEQ ID: NO 10
   1 AGGAAACAGC TATGAACGTT

SEQ ID: NO 11
   1 ACTGAAAGCTT TACTTTCATC ACAAGCCTCT

SEQ ID: NO 12
   1 ACTGAAAGCTT AGATTCAGCG CGAGAGTGAT

SEQ ID: NO 13
   1 ACTGAAAGCT TTTTAATTGT GTGACCACTA T
```

What is claimed is:

1. A stabilized recombinant expression plasmid vector comprising:
   a polynucleotide encoding an antitoxin gene which expresses a polypeptide that counteracts a polypeptide toxic to a host cell, the toxic polypeptide being expressed by a toxin gene in the host cell, and
   a polynucleotide encoding a polypeptide expression product, wherein:
      the stabilized recombinant expression plasmid vector is derived from a *Hafnia alvei* autonomously replicable backbone plasmid; and
      the antitoxin gene and the toxin gene comprise an antitoxin/toxin gene pair originated from *Hafnia alvei*.

2. The recombinant expression plasmid vector of claim 1, further comprising a polynucleotide encoding the toxin gene.

3. The recombinant expression plasmid vector of claim 1, wherein the backbone plasmid is selected from the group consisting of pUC, pUC18/19, pBR322, pACYC and any derived plasmids thereof.

4. The recombinant expression plasmid vector of claim 1, wherein the polypeptide expression product is an enzyme selected from the group consisting of decarboxylase, hydrolases and phosphorylase.

5. The recombinant expression plasmid vector of claim 4, wherein the decarboxylase is an amino acid decarboxylase selected from the group consisting of lysine decarboxylase, tyrosine decarboxylase, arginine decarboxylase, ornithine decarboxylase, and glutamate decarboxylase.

6. The recombinant expression plasmid vector of claim 5, wherein the polynucleotide encoding lysine decarboxylase comprises a polynucleotide selected from the group consisting of haldc gene, cadA gene, and fragments thereof.

7. The recombinant expression plasmid vector of claim 2, wherein the backbone plasmid is selected from the group consisting of pUC, pUC18/19, pBR322, pACYC and any derived plasmids thereof.

8. The recombinant expression plasmid vector of claim 2, wherein the polypeptide expression product is an enzyme selected from the group consisting of decarboxylase, hydrolases and phosphorylase.

9. The recombinant expression plasmid vector of claim 8, wherein the decarboxylase is an amino acid decarboxylase selected from the group consisting of lysine decarboxylase, tyrosine decarboxylase, arginine decarboxylase, ornithine decarboxylase, and glutamate decarboxylase.

10. The recombinant expression plasmid vector of claim 9, wherein the polynucleotide encoding lysine decarboxylase comprises a polynucleotide selected from the group consisting of haldc gene, cadA gene, and fragments thereof.

11. A transformant obtained by transforming a recombinant expression plasmid vector of claim 1 into a host cell, wherein the host cell is a *Hafnia alvei* strain free of endogenous plasmids.

12. The transformant of claim 11, wherein the *Hafnia alvei* strain is an industrial *Hafnia alvei* strain.

13. A method of producing cadaverine (1,5-pentanediamine) comprising:
   1a) cultivating the transformant of one of claim 7;
   1b) producing cadaverine using the culture obtained from step 1a to decarboxylate lysine; and
   1c) extracting and purifying cadaverine from the reaction obtained from step 1b.

14. A method of preparing 1,5-diisocyanatopentane comprising:
   2a) preparing biobased cadaverine according to the method of claim 13; and
   2b) converting biobased cadaverine obtained from step 2a to 1,5-diisocyanatopentane.

* * * * *

SEQUENCE LISTING

<160> NUMBER OF SEQ ID NOS: 13

<210> SEQ ID NO 1
<211> LENGTH: 1333
<212> TYPE: DNA
<213> ORGANISM: Hafnia alvei

<400> SEQUENCE: 1

```
ttgactttgt taaaagtcag gcataagatc aaaatactgt atatataaca atgtatttat        60
atacagtatt ttatactttt tatctaacgt cagagagggc aatattatga gtggtggaga       120
tggcaagggt cacaatagtg gagcacatga ttccggtggc agcattaatg gaacttctgg       180
gaaaggtggg ccatcaagcg gaggagcatc agataattct gggtggagtt cggaaaataa       240
cccgtggggc ggtggtaact cgggaatgat tggtggcagt caaggaggta acggagctaa       300
tcatggtggc gaaatacat cttctaacta tgggaaagat gtatcacgcc aaatcggtga       360
tgcgatagcc agaaaggaag gcatcaatcc gaaaatattc actgggtact ttatccgttc       420
```

```
agatggatat tgatcggaa taacgccact tgtcagtggt gatgcctttg gcgttaatct      480
tggcctgttc aataacaatc aaaatagtag tagtgaaaat aagggatgga atggaaggaa      540
tggagatggc attaaaaata gtagccaagg tggatggaag attaaaacta atgaacttac      600
ttcaaaccaa gtagctgctg ctaaatccgt tccagaacct aaaaatagta atattataa       660 gtccatgaga gaagctagcg atgaggttat taattctaat ttaaaccaag gcatggagt       720 tggtgaggca gctagagctg aaagagatta cagagaaaaa gtaaagaacg caatcaatga      780
taatagtccc aatgtgctac aggatgctat taaatttaca gcagattttt ataaggaagt      840 tttaacgct tacggagaaa aagccgaaaa actagccaag ttattagctg atcaagctaa       900
aggtaaaaag atccgcaatg tagaagatgc attgaaatct tatgaaaaac acaaggctaa      960
cattaacaaa aaaatcaatg cgaaagatcg cgaagctatc gccaaggctt tggagtctat     1020
ggatgtagaa aaagccgcaa aaatatatc caagttcagc aaaggactag gttgggttgg     1080
cccagctatc gatataactg attggtttac agaattatac aaagcagtga aaactgataa     1140
ttggagatct ctttatgtta aaactgaaac tattgcagta gggctagctg caacccatgt     1200
caccgcctta gcattcagtg ctgtcttggg tgggcctata ggtattttag gttatggttt     1260
gattatggct ggggttgggg cgttagttaa cgagacaata gttgacgagg caaataaggt     1320
cattgggatt taa                                                       1333

<210> SEQ ID NO 2
<211> LENGTH: 336
<212> TYPE: DNA
<213> ORGANISM: Hafnia alvei

<400> SEQUENCE: 2
ctatatttta gcggtcacat tttttatttc aaaacaaaca gaaagaacac caataggaat       60
tgatgtcata aaaataaaaa taaaatacaa agtcattaaa tatgttttg gcacaccatc       120 cttaaaaaaa cctgttttcc aaaattcttt tttcgtatat ctaagcgctg ctttctctat      180
tagaaaccga gagaaaggaa atagaatagc gctagccaaa ccaaagattc tgagcgcaat      240
tattttaggt tcgtcatcac cataactggc gtaaagaata caagcagcca taaagtatcc      300
ccaaaacata ttatgtatgt aatatttcct tgtcat                               336

<210> SEQ ID NO 3
<211> LENGTH: 1077
<212> TYPE: DNA
<213> ORGANISM: Hafnia alvei

<400> SEQUENCE: 3
atgagtggtg gagacggtaa aggtcacaat agtggagcac atgattccgg tggcagcatt       60
aatggaactt cggggaaagg tggacctgat tctggtggcg gatattggga caaccatcca      120
catattacaa tcaccggtgg acgggaagta ggtcaagggg gagctggtat caactggggt      180
ggtggttctg gtcatggtaa cggcgggggc tcagttgcca tccaagaata taacacgagt      240
aaatatccta acacgggagg atttcctcct cttggagacg ctagctggct gttaaatcct      300 ccaaatggt cggttattga agtaaaaatca gaaaactcag catggcgctc ttatattact      360
catgttcaag gtcatgttta caaattgact tttgatggta cgggtaagct cattgatacc      420
gcgtatgtta attatgaacc cagtgatgat actcgttgga gcccgcttaa aagttttaaa      480
tataataaag gaaccgctga aaacaggtt agggatgcca ttaacaatga aaagaagca       540 gttaaggacg ctgttaaatt tactgcagac ttctataaag aggttttaa ggtttacgga      600
```

```
gaaaaagccg agaagctcgc taagttatta gcagatcaag ctaaaggcaa aaggttcgc     660 aacgtagaag atgccttgaa atcttatgaa aaatataaga ctaacattaa caaaaaaatc    720
aatgcgaaag atcgcgaagc tattgctaaa gccttggagt ctatggatgt aggaaaagcc    780
gcaaaaaata tagccaagtt cagtaaagga ctaggttggg ttggccctgc tatcgatata    840
actgattggt ttacagaatt atacaaggca gtggaaactg ataattggag atcttttat    900 gttaaaactg aaactattgc agtagggcta gctgcaaccc atgttgccgc cttggcattc    960
agcgctgtct tgggtgggcc tgtaggtatt ttgggttatg gtttgattat ggctggggtt   1020
ggggcgttag ttaatgagac aatagttgac gaggcaaata aggttattgg gcttaa       1077
```

```
<210> SEQ ID NO 4
<211> LENGTH: 336
<212> TYPE: DNA
<213> ORGANISM: Hafnia alvei

<400> SEQUENCE: 4
ctataattta gcggtcacat ttttatttc aaaaaaaaca gaaataacac ctataggaat      60
tgatgtcata aaaataaaaa ttaaatacaa agtcattaaa tatgttttg gcacgccatc     120 cttaaaaaaa ccagtttccc aaaattcttt ttcgtatat ctaagcgcgg ttttctctat     180
taaaaaccga gagaaaggga ataggatagc actagccaaa ccaaagattc tgagcgcaat    240
tattttaggt tcgttatccc cataactggc gtaaagaata caaacagcca taaagtaccc    300
ccaaaacata ttatgtatat aatatttcct tgtcat                              336
```

```
<210> SEQ ID NO 5
<211> LENGTH: 2148
<212> TYPE: DNA
<213> ORGANISM: Escherichia coli

<400> SEQUENCE: 5
atgaacgtta ttgcaatatt gaatcacatg ggggtttatt ttaaagaaga acccatccgt     60
gaacttcatc gcgcgcttga acgtctgaac ttccagattg tttacccgaa cgaccgtgac    120 gactattaa aactgatcga aaacaatgcg cgtctgtgcg gcgttatttt tgactgggat    180
aaatataatc tcgagctgtg cgaagaaatt agcaaaatga cgagaacct gccgttgtac    240 gcgttcgcta atacgtattc cactctcgat gtaagcctga tgacctgcg tttacagatt    300 agcttctttg aatatgcgct gggtgctgct gaagatattg ctaataagat caagcagacc    360
actgacgaat atatcaacac tattctgcct ccgctgacta agcactgtt taaatatgtt    420 cgtgaaggta aatatacttt ctgtactcct ggtcacatgg gcggtactgc attccagaaa    480
agcccggtag gtagcctgtt ctatgatttc tttggtccga ataccatgaa atctgatatt    540
tccatttcag tatctgaact gggttctctg ctggatcaca gtggtccaca caaagaagca    600
gaacagtata tcgctcgcgt cttaacgca gaccgcagct acatggtgac caacggtact    660
tccactgcga acaaaattgt tggtatgtac tctgctccag caggcagcac cattctgatt    720
gaccgtaact gccacaaatc gctgacccac ctgatgatga tgagcgatgt tacgccaatc    780
tatttccgcc cgacccgtaa cgcttacggt attcttggtg tatcccaca gagtgaattc    840 cagcacgcta ccattgctaa gcgcgtgaaa gaaacaccaa acgcaacctg gccggtacat    900
gctgtaatta ccaactctac ctatgatggt ctgctgtaca caccgacttc atcaagaaa    960 acactggatg tgaaatccat ccactttgac tccgcgtggg tgccttacac caacttctca   1020
```

```
ccgatttacg aaggtaaatg cggtatgagc ggtggccgtg tagaagggaa agtgatttac      1080
gaaacccagt ccactcacaa actgctggcg gcgttctctc aggcttccat gatccacgtt      1140
aaaggtgacg taaacgaaga aacctttaac gaagcctaca tgatgcacac caccacttct      1200
ccgcactacg gtatcgtggc gtccactgaa accgctgcgg cgatgatgaa aggcaatgca      1260
ggtaagcgtc tgatcaacgg ttctattgaa cgtgcgatca aattccgtaa agagatcaaa      1320
cgtctgagaa cggaatctga tggctggttc tttgatgtat ggcagccgga tcatatcgat      1380
acgactgaat gctggccgct gcgttctgac agcacctggc acggcttcaa aaacatcgat      1440
aacgagcaca tgtatcttga cccgatcaaa gtcaccctgc tgactccggg gatggaaaaa      1500
gacggcacca tgagcgactt tggtattccg gccagcatcg tggcgaaata cctcgacgaa      1560
catggcatcg ttgttgagaa aaccggtccg tataacctgc tgttcctgtt cagcatcggt      1620
atcgataaga ccaaagcact gagcctgctg cgtgctctga ctgactttaa acgtgcgttc      1680
gacctgaacc tgcgtgtgaa aaacatgctg ccgtctctgt atcgtgaaga tcctgaattc      1740
tatgaaaaca tgcgtattca ggaactggct cagaatatcc acaaactgat tgttcaccac      1800
aatctgccgg atctgatgta tcgcgcattt gaagtgctgc cgacgatggt aatgactccg      1860
tatgctgcat tccagaaaga gctgcacggt atgaccgaag aagtttacct cgacgaaatg      1920
gtaggtcgta ttaacgccaa tatgatcctt ccgtacccgc cgggagttcc tctggtaatg      1980
ccgggtgaaa tgatcaccga agaaagccgt ccggttctgg agttcctgca gatgctgtgt      2040
gaaatcggcg ctcactatcc gggctttgaa accgatattc acggtgcata ccgtcaggct      2100
gatggccgct ataccgttaa ggtattgaaa gaagaaagca aaaaataa                   2148

<210> SEQ ID NO 6
<211> LENGTH: 2220
<212> TYPE: DNA
<213> ORGANISM: Hafnia alvei

<400> SEQUENCE: 6
atgaatatca ttgccatcat gaacgattta agcgcttatt ttaaggaaga acccctgcgc      60
gagctgcatc aagagttaga gaaggaaggc ttccgtattg cttatcccaa agaccgcaac      120
gatctgctga agctgattga aaacaactcc gcctgtgtg gcgtcatttt cgactgggat      180
aaatataacc tcgaactcag cgctgaaatc agcgagctca acaaactgct gccaatttat      240
gccttcgcca ataccattc gacgcttgac gtcaacatga gcgacctgcg tcttaatgtt      300
cgcttctttg aatatgcatt aggcagcgcg caagacattg ccaccaagat ccgccaaagc      360
accgatcagt atattgatac cattctgcca ccgctgacca aggcgctgtt caaatacgtc      420
aaagaagaga aatacacagt ctgtacgccg gggcatatgg gcggaactgc gttcgataaa      480
agccctgtcg gtagcctgtt ctatgatttc ttcggtgaaa acaccatgcg ttcggatatc      540
tcgatctccg tatctgagct cggatcgctg ctcgatcata gcggcccaca ccgtgacgcc      600
gaagagtata tcgcgcgcac gttcaacgcc gatcgcagct atatcgtaac caacggaaca      660
tctacggcga ataaaattgt cggcatgtat tcatctcctg ccggtgccac tattctgata      720
gaccgtaact gccataaatc attgaccat ttgatgatga tgagcaacgt tgtccccgtc      780
tatctgcgcc caacccgtaa cgcctacggc attttaggcg ggataccgca aagcgagttc      840
acccgcgcca gcattgaaga gaaagtgaaa aatacgccca atgcgacatg gccggtgcat      900
gcggtagtca ccaactctac ctatgacggc ctgttctaca ataccgaata catcaaaaac      960
acgcttgatg ttaagtcgat tcacttcgat tcggcatggg tgccttacac caacttccat      1020
```

```
ccgatttacc aaggcaaagc agggatgagc ggtgaacgtg tgccggggaa aatcatctac    1080
gagactcagt ccacccacaa actgctggcg gcattctcgc aggcatcgat gatccacgtg    1140
aaaggtgaga tcaacgaaga aaccttcaat gaagcctata tgatgcatac ctcaacatca    1200
ccgcattacg ggatcgttgc gtcgacggaa accgcggcgg ctatgatgaa gggcaacgcc    1260
ggtaagcgtt taattaacgg ttcaattgaa cgagcgatcc gcttccgtaa agagatccgc    1320
cgcttacgta cagaatctga tggctggttc tttgacgtat ggcagccgga taacattgac    1380
gaggttgctt gctggccact caatccacgt aatgaatggc atggattccc gaacatcgac    1440
aacgatcata tgtatcttga tccgatcaaa gtcactctgc tgaccccagg tttaagcccc    1500
aatggcactc tggaagagga agggataccg gcgtcgatcg tgtcgaaata tctggatgag    1560
cacggcatca tcgtggaaaa aaccgggcca tataacctgc tcttcctgtt tagtatcggg    1620
atcgataaaa ccaaggcgtt gagcttgttg cggcattaa ccgatttcaa acgcgtgtat    1680
gacctcaacc tgcgcgtgaa aaacgtgttg ccatcgctct ataacgaggc gcctgatttc    1740
tataaagaga tgcgaattca ggagttggct caggggattc atgctctggt gaaacaccac    1800
aatctaccag acctgatgta tcgtgcattt gaggtattac caaagctggt gatgacgccg    1860
catgatgcgt tccaagaaga agtgcgtggc aatattgagc catgtgcctt ggatgatatg    1920
ttagggaaag ttagcgccaa catgatcttg ccgtatcctc cgggtgttcc ggtggttatg    1980
ccgggagaaa tgctcactaa ggagagccgc cctgttctga gcttcttgca gatgctatgt    2040
gaaattggcg cacactatcc gggctttgaa acggatattc acggcgttca tcgtgatggt    2100
gcaacgggta aatacatggt cgtggtgctc aaacaaggcg cagatgaacc gggtgataaa    2160
ccgagtgata cggtgaagaa agcgccgggt aaaaaaccat cagcggcgaa gaagtcataa    2220
```

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7

```
atgaacgtta ttgcaatatt                                                 20
```

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8

```
actgaaagct tccacttccc ttgtacgagc t                                    31
```

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9

```
attcaatatt gcaataacgt tcatagctgt ttcctgtgtg                           40
```

<210> SEQ ID NO 10

```
<211> LENGTH: 20
<212> TYPE: DNA
<213> ORGANISM: Artificial Sequence
<220> FEATURE:
<223> OTHER INFORMATION: primer

<400> SEQUENCE: 10
aggaaacagc tatgaacgtt                                               20

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
actgaaagct ttactttcat cacaagcctc t                                  31

<210> SEQ ID NO 12
<211> LENGTH: 31
<212> TYPE: DNA
<213> ORGANISM: Artificial Sequence
<220> FEATURE:
<223> OTHER INFORMATION: primer

<400> SEQUENCE: 12
actgaaagct tagattcagc gcgagagtga t                                  31

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
actgaaagct ttttaattgt gtgaccacta t                                  31
```